United States Patent [19]
Tahara et al.

[11] Patent Number: 6,069,136
[45] Date of Patent: May 30, 2000

[54] BACTERIAL CELLULOSE CONCENTRATE AND METHOD FOR THE TREATMENT OF THE CONCENTRATE

[75] Inventors: Naoki Tahara; Kunihiko Watanabe; Nobuya Hioki; Yasushi Morinaga; Tadahiko Hajouda; Hiroshi Miyashita; Akira Shibata; Hiroshi Ougiya, all of Kawasaki, Japan

[73] Assignee: Bio-Polymer Research Co., Ltd., Kawasaki, Japan

[21] Appl. No.: 08/983,323

[22] PCT Filed: May 26, 1997

[86] PCT No.: PCT/JP97/01785

§ 371 Date: Mar. 16, 1998

§ 102(e) Date: Mar. 16, 1998

[87] PCT Pub. No.: WO97/45452

PCT Pub. Date: Dec. 4, 1997

[30] Foreign Application Priority Data

May 24, 1996  [JP]  Japan .................................. 8-151860

[51] Int. Cl.[7] .............................. A61K 31/70; C07H 1/00; C08B 16/00
[52] U.S. Cl. ................................ 514/57; 536/56; 536/124
[58] Field of Search .......................... 536/56, 124; 514/57

[56] References Cited

U.S. PATENT DOCUMENTS

| 4,861,427 | 8/1989 | Johnson et al. | ......................... 162/129 |
|---|---|---|---|
| 4,960,763 | 10/1990 | Stephens et al. | ......................... 514/57 |
| 5,637,197 | 6/1997 | Watt et al. | ............................... 162/202 |

*Primary Examiner*—Elli Peselev
*Attorney, Agent, or Firm*—Oblon, Spivak, McClelland, Maier & Neustadt, P.C.

[57] ABSTRACT

The purpose of the present invention is to provide a simple and economical method for the production of BC having improved properties such as dispesibility, suspensibility and viscosity.

The present invention relates to a method for the improvement of dispersibility and suspensibility of bacterial cellulose, comprising concentrating an aqueous suspension of bacterial cellulose to a final concentration of the bacterial cellulose of between 10% by weight or more and less than 75% by weight, dispersing it again into an aqueous solution and homogenizing the bacterial cellulose in the resulting dispersion, to a method for the improvement of paper properties of bacterial cellulose, comprising concentrating an aqueous suspension of homogenized bacterial cellulose to a final concentration of the bacterial cellulose of between 4% by weight or more and less than 75% by weight, dispersing it again into an aqueous solution and homogenizing the bacterial cellulose in the resulting dispersion, and to the BC concentrate thus prepared.

9 Claims, No Drawings

6,069,136

BACTERIAL CELLULOSE CONCENTRATE AND METHOD FOR THE TREATMENT OF THE CONCENTRATE

TECHNICAL FIELD

This invention relates to a concentrate of cellulosic material (bacterial cellulose: "BC") which may be produced by culturing cellulose-producing bacteria, to a method for the improvement of dispersibility and suspensibility, and to a method for the improvement of properties of paper.

BACKGROUND ART

Since the bacterial cellulose is edible as well as tasteless and odorless, it is utilized in the food industry. The homogenized bacterial cellulose's high dispersibility in water further provides it with many industrial applications, such as to maintain particle sizes of food, cosmetics or coating agents, to strengthen food materials, to maintain moisture, to improve stability of food, and to be used as low-calorie additives and an emulsion stabilizer.

The bacterial cellulose is characterized by a sectional width of its fibrils which is smaller by two orders of magnitude than that of other kinds of cellulose fibers such as those derived from wood pulp.

Due to such structural and physical feature of microfibril, a homogenized bacterial cellulose has plenty of industrial applications as a strengthening agent for polymers, especially hydrophilic polymers. Products prepared by solidification of the homogenized bacterial cellulose in the form of a lump or paper show a high elastic modulus in tension owing to the above feature, and are therefore expected to have excellent mechanical properties for use in various kinds of industrial materials.

However, since an aqueous suspension or dispersion of the homogenized BC contains solvent such as water in an amount of a few to a few hundreds times the amount of cellulose component, it has some disadvantages such as the increase of space for storage, increase of the costs for storage and transportation, and decomposition of cellulose by bacteria during storage.

The present inventors have already proposed a method for drying of bacterial cellulose, comprising adding a third component other than water or BC to the aqueous BC suspension and dehydrating and drying (Japanese Patent Application Hei 7 (1995)-329472). According to this method, properties of BC such as solubility, dispesibility, precipitation degree and viscosity may be recovered when BC is returned from its dry state (water content is 25% by weight or less) to its aqueous suspension.

Although BC is used as an additive for paper, especially for the purpose of an improvement in yield on fillers, it will disadvantageously reduce its freeness in papermaking.

The present inventors have studied simple and economical methods for the production of BC having improved properties such as dispesibility, suspensibility and viscosity, so as to solve the above problems, and finally complete the present invention.

DISCLOSURE OF INVENTION

The present invention relates to a bacterial cellulose concentrate containing unhomogenized bacterial cellulose in an amount of the range between 10% by weight or more and less than 75% by weight, preferably between 25% by weight or more and less than 70% by weight.

The present invention also relates to a bacterial cellulose concentrate containing homogenized bacterial cellulose in an amount of the range between 4% by weight or more and less than 75% by weight, preferably between 10% by weight or more and less than 75% by weight.

Further, the present invention relates to a method for the improvement of dispersibility and suspensibility of bacterial cellulose, comprising concentrating an aqueous suspension of bacterial cellulose to a final concentration of the bacterial cellulose of between 10% by weight or more and less than 75% by weight, dispersing it again into an aqueous solution and homogenizing the bacterial cellulose in the resulting dispersion. The present invention accordingly relates to the aqueous suspension of bacterial cellulose thus prepared.

Further, the present invention relates to a method for the improvement of dispersibility and suspensibility of bacterial cellulose, comprising concentrating an aqueous suspension of homogenized bacterial cellulose to a final concentration of the bacterial cellulose of between 4% by weightor more, preferably 6% by weight or more and less than 75% by weight, dispersing it again into an aqueous solution and homogenizing the bacterial cellulose in the resulting dispersion. The present invention accordingly relates to the aqueous suspension of the homogenized bacterial cellulose thus prepared.

The homogenization may be carried out by mechnical shearing stress, ultrasonic generator, high-pressure treatment, hydrolysis with an acid or enzyme, or bleach, or combination thereof.

The bacterial cellulose concentrate or the aqueous suspension or dispersion of the bacterial cellulose may contain third components such as those disclosed in the Japanese Patent Application Hei 7 (1995)-329472, for example, hydrophilic liquid such as glycerin, ethylene glycol, dimethyl sulfoxide, dimethyl formamide, surfactants, lactic acid, gluconic acid and δ-gluconolactone and combination thereof; water-soluble substance such as low-molecular compounds or high-molecular compounds; and hydrophilic solid such as water-insoluble compounds and hardly water-soluble compounds.

An amount of the third component to be added may be optionally determined by those skilled in the art, depending on the kind of the material and the like, being usually in the range of from 2% by weight to 1,000% by weight of BC.

Further, the culture media of cellulose-producing bacteria per se or those further containing the third component may be used as an example of the above aqueous suspension of the bacterial cellulose. The concentration of bacterial cellulose in the aqueous suspension is significantly lower than that in the concentrate, i.e., usually between 0.01% by weight and 3% by weight, which may be optionally selected by those skilled in the art.

The concentrate according to the present invention may be prepared by dehydration with any known means such as a filter press, belt-press, centrifugation, aspirator or drying. The concentration step of the present method may be also carried out in the same way as above.

The above drying may be also carried out by any known methods such as spray-dry, drying in the air, drying with a dryer and drying under vacuum.

The homogenization of bacterial cellulose is considered to be a phenomenon in which the cellulose is deformed and broken under a stress induced inside the cellulose by an external force such as a mechanical force. Accordingly, the homogenization of the bacterial cellulose may be carried out by externally applying the mechanical force to the bacterial cellulose.

The mechanical force includes tensile stress, bending stress, compressive stress, torsional stress, impact stress and shearing stress. Compressive stress, impact stress and shearing stress are generally dominating.

A practical application of these mechanical forces to the bacterial cellulose may be achieved by using an appropriate apparatus such as a cooking mixer, homogenizer, blender, Polytron or ultrasonic generator.

In the homogenization using the above apparatus, the mechanical force is mainly composed of the impact force generated from the collision between agitating blades and the bacterial cellulose, and of the shearing force generated due to differences of the speed in the medium.

In the homogenization using Polytron, the mechanical force is mainly composed of the compressive force generated by sandwiching the bacterial cellulose between outer blades and inner blades, of the impact force generated from the collision between the bacterial cellulose and blades rotating at a high speed, and of the shearing stress generated in the suspension at a space between stopping outer blades and inner blades rotating at a high speed.

In the homogenization using the ultrasonic generator, the mechanical force is mainly composed of a strong shearing stress locally generated by a continuous cavitation in the suspension due to the oscillation of the ultrasonic generator.

In addition to the above embodiments, the present homogenization may be carried out in any manner for externally applying a certain load (mechanical force) to the bacterial cellulose.

Those skilled in the art may optionally select other homogenization conditions.

It is obvious for those skilled in the art that the present homogenization is not limited to only a secondary or an independent treatment on the bacterial cellulose obtained after an agitated culture of cellulose-producing microorganisms (bacteria) and the subsequent separation and purification of the cellulose from its culture medium.

Since the agitation operation may homogenize the bacterial cellulose, as mentioned below, it is fully possible to homogenize the bacterial cellulose by the agitation operation during the agitated culture according to the present invention.

Further, the separation, washing, purification and transporting operations may also homogenize the bacterial cellulose, and therefore the additional homogenization in these operations may be included in the homogenization of the present invention.

The cellulose-producing bacteria used in the present invention may include Acetobacter strains such as *Acetobacter xylinum* subsp. sucrofermentans such as BPR 2001 strain, *Acetobacter xylinum* ATCC23768, *Acetobacter xylinum* ATCC23769, *Acetobacter pasteurianus* ATCC10245, *Acetobacter xylinum* ATCC14851, *Acetobacter xylinum* ATCC11142, *Acetobacter xylinum* ATCC10821; Agrobacterium; Rhizobium; Sarcina; Pseudomonas, Achromobacter; Alcaligenes; Aerobacter; Azotobacter; and Zooglea; and any mutants prepared by the treatment for mutagenesis with a known method using mutagens such as NTG (nitrosoguanidine).

The BPR 2001 has been deposited at the National Institute of Bioscience and Human-Technology, Agency of Industrial Science and Technology (1–3, Higashi 1-chome, Tsukuba-shi, Ibaraki-ken 350 Japan) on Feb. 24, 1993 under accession number FERM P-13466, and then transferred on Feb. 7, 1994 to the deposit under the terms of the Budapest Treaty on the International Recognition of the Deposit of Microorganisms for the Purposes of Patent Procedure and Regulation under accession number FERM BP-4545.

The chemical mutagenesis treatment using the mutagens such as NTG is described in, for example, Japanese Patent Application Hei 6(1994)-127994, Bio Factors, Vol. 1, pp.297–302 (1988) and J. Gen. Microbiol, Vol. 135, pp.2917–2929 (1989). Accordingly, those skilled in the art may obtain the present mutants in accordance with these known methods. The present mutants may be also obtained by other treatments such as application of radioactive rays.

One of the preferred examples may be a strain producing a bacterial cellulose having a weight-average degree of polymerization in terms of polystyrene of $1.6 \times 10^4$ or above, preferably $1.7 \times 10^4$ or above, which may be produced in the aerobic agitated culture; a bacterial cellulose having a weight-average degree of polymerization in terms of polystyrene of $2.0 \times 10^4$ or above, which may be produced in a static culture.

One example of the above bacteria producing bacterial cellulose with a high-degree of polymerization, BPR3001A, has been deposited at the National Institute of Bioscience and Human-Technology, Agency of Industrial Science and Technology (1-3, Higashi 1-chome, Tsukuba-shi, Ibaraki-ken 350 Japan) on Jun. 12, 1995 under accession number FERM P-14982, and then transferred on Feb. 23, 1996 to the deposit under the terms of the Budapest Treaty on the International Recognition of the Deposit of Microorganisms for the Purposes of Patent Procedure and Regulation under accession number FERM BP-5421.

It is well known that the higher the degree of polymerization is, the higher the strength and elasticity of the polmer materials become. The same is true for bacterial cellulose. The articles made from the bacterial cellulose with a high degree of polymerization will show increased strength and elasticity compared those made from the bacterial cellulose with a relatively low degree of polymerization. Thus, the bacterial cellulose with a high degree of polymerization may be advantageously used for the preparation of the articles having a high strength and elasticity.

The weight-average degree of polymerization of a various kinds of cellulose such as BC of this invention may be determined by the method using a GPC system (Tosoh HLC-8020) equipped with an RI detector as follows:

A cellulose sample is nitrated with a fuming nitric acid-phosphorous pentaoxide solution according to the method of W. J. Alexander, R. L. Mitchell, Analytical Chemistry 21, 12, 1497–1500 (1949).

Nitrated cotton linter is used as a control.

Nitrated cellulose is then dissolved in THF (Wako Pure Chemical Industries Ltd., the first grade) to a final concentration of 0.05%, and filtered through a 1.0 $\mu$m pore-size filter. THF is also used for an elution solvent.

The flow rate, pressure, and sample-injection volume are adjusted to be 0.5 ml/min., 10~13 kgf/cm$^2$ and 100 $\mu$l, respectively.

The column system consists of two TSKgel GMH-HR (S) columns (7.5 ID×300 mm) and a guard column (Tosoh Co., Ltd.). The analysis is carried out at a temperature of 35° C.

A relative molecular weight in terms of polystyrene is calculated by using polystyrene standards (Tosoh).

The polystyrene standards having a molecular weight in the range of $2.0 \times 10^7$ to 2630 are used and a standard curve is prepared based on the following three-dimension approximate equation:

$$\log M = At^3 + Bt^2 + Ct + D$$

wherein "t" is an elution time and "M" is a molecular weight.

The weight-average molecular weight and number-average molecular weight are calculated by a program (ver. 3, 10) equipped in a data processor (SC-8020).

The weight-average degree of polymerization of the original cellulose samples is finally calculated based on the above data, taking substitution degrees after the nitration into consideration.

Carbon sources in the culture media useful in the present invention include sucrose, glucose, fructose, mannitol, sorbitol, galactose, maltose, erythritol, glycerol, ethyleneglycol, ethanol and their mixtures. In addition, sucrose may be combined with starch hydrolysate containing these carbon sources, citrus molasses, beet molasses, squeezed juice from beet or sugar cane, juice from citrus and the like.

Nitrogen sources useful in the present invention include organic or inorganic ones such as ammonium salts including ammonium sulfate, ammonium chloride, ammonium phosphate; nitrates; and urea. Nitrogen-containing natural nutrients may be also used including Bacto-Peptone, Bacto-soytone, Yeast-Extract and Bean-Condensate.

A trace amount of organic nutrients may be further added including amino acids, vitamins, fatty acids, nucleic acids, 2,7,9-tricarboxy-1H pyrrolo [2,3,5]-quinoline-4,5-dione, sulfite pulp waste liquor, lignin sulfonic acid and the like.

When the mutants with the nutritional requirement for amino acids are used, such required nutrients should be supplemented in the culture media. Inorganic nutrients include phosphate salts, magnesium salts, calcium salts, iron salts, manganese salts, cobalt salts, molybdate salts, hematite salts, chelate metal salts and the like.

It is also possible to optionally supply accelerators for the cellulose production such as inositol, phytic acid, pyrroloquinoline quinone (PQQ) (Japanese Patent Publication Hei 5(1993)-1718; Mitsuo TAKAI, Japan TAPPI Journal, Vol.42, No.3, pp.237–244), carboxylic acid or their salts (Japanese Patent Laid-Open Application Hei 7(1995)-39386, laid open Feb. 10, 1995), invertase (Japanese Patent Laid-Open Application Hei 7(1995)-184677, laid open Jul. 25, 1995) and methionine (Japanese Patent Laid-Open Application Hei 7(1995)-184675, laid open Sep. 25, 1995) into the culture media.

For example, when the Acetobacter is used as the cellulose-producing bacteria, a pH range for the culture is controlled between 3 and 7, preferably around 5. A culture temperature is kept in a range between 10 and 40° C., preferably between 25 and 35° C. Oxygen supply into a culturing apparatus may contain from 1 to 100% oxygen, desirably 21 to 80%. Those skilled in the art may optionally determine the contents of these components in the culture media and amounts of the bacteria to be inoculated into the media, depending on the culture method to be used.

The present method may be carried out in known culture conditions such as the static culture and aerobic agitated culture, as described above. Any known culture operation method such as batch fermentation, fed batch fermentation, repeated batch fermentation and continuous fermentation may be adopted.

The agitated culture is carried out under agitation of the culture medium. Said agitation operation during the agitated culture may change the structure of the bacterial cellulose into, for example, an more amorphous one having a lower crystallinity.

Means for agitation include impellers, air-lift fermenters, pump-driven recirculation of the fermenter broth and any combination of these means.

Further, the bacterial cellulose may be also produced by the method described in Japanese Patent Laid-Open Application Hei 8(1996)-33494 (laid open Feb. 6, 1996) in the name of the present applicant, wherein culture media containing bacteria are circulated between a culturing apparatus and a separator to separate the resulting bacterial cellulose from the bacteria and culture media in said separator, or by the method described in Japanese Patent Laid Open Application Hei 8(1996)-33495 (laid open Feb. 6, 1996) in the name of the present applicant, wherein the concentration of the bacterial cellulose in culture media is kept at a lower level by a continuous removal of the culture media from its culture system and a continuous supply of fresh culture media having almost the same volume as the removed culture media.

The agitated culture may be carried out in any culturing apparatus with agitation, such as a jar fermenter, tank, baffle flask, inclined-neck flask and air-lift fermenter.

In the present agitated culture, gas may be optionally passed through the culture media. Such gas includes oxygen-containing gas such as air, as well as gas free of oxygen such as argon or nitrogen. Those skilled in the art may optionally select the gas to be passed, depending on the culture conditions.

For example, when anaerobic bacteria are used, an inert gas may be passed through the culture media so that the bubbles thereof will agitate the culture media.

When aerobic bacteria are used, an oxygen-containing gas may be passed through the culture media to supply oxygen required for the growth of the bacteria. The bubbles thereof will also agitate the culture media.

The bacterial cellulose obtained in the agitated culture may be separated from the culture media by using the centrifugation or filtration method.

The bacterial cellulose may be recovered together with the bacteria, and then impurities other than the bacterial cellulose, including the bacteria per se, may be removed from the recovered bacterial cellulose.

The impurities may be almost completely removed from the bacterial cellulose by washing, dehydration under pressure, dilute acid washing, alkali washing, bleaching with hypochlorite soda or hydrogen peroxide, lysing with lytic enzymes such as lysozyme, treatment with surfactants such as sodium lauryl sulfate or sodium deoxycholate, washing under heat at a temperature range between a room temperature and 200° C., and any combination of these treatments.

The bacterial cellulose thus obtained according to the present invention includes cellulose, those comprising heteropolysaccharides having cellulosic main chains, and those comprising β-1,3- or β-1,2-glucan. Said heteropolysaccharides contain as components hexoses, pentoses and organic acids such as mannose, fructose, galactose, xylose, arabinose, rhamnose and glucuronic acid, as well as glucose.

These polysaccharides may be present alone or as a mixture combined each other via hydrogen bonds.

BEST MODE FOR CARRYING OUT THE INVENTION

The present invention will be further illustrated by the following examples, which should not be construed to limit the scope of the present invention. In the following examples, the BC content (%) means the 37% by weight" unless particularly otherwise remarked.

The properties are determined as follows.

Dispersibility:

Dispersibility of the suspension of the homogenized BC is observed and compared with the naked eye before and after drying.

Precipitation Degree after Centrifugation:

Precipitation degree is represented in terms of a volume ratio of a precipitated bacterial cellulose to the total volume, after the aqueous suspension (10 ml) containing 0.2% of BC in a tube (15 ml, Falcon) is centrifuged at 3,000 rpm for 15 minutes. The greater the value of precipitation degree shows, the higher dispersibility is, meaning that the suspended BC will hardly precipitate and be dispersed well.

Viscosity:

The "viscosity" in the present sepcification means an absolute value of complex viscosity that is obtained with respect to the aqueous suspension of BC (0.1%) in a dynamic liquid viscoelasticity measuring apparatus "FLUIDS SPECTROMETER RFS II" (Rheometric Scientific Ltd.) at an angular frequency of 10 rad/sec and 30° C., and shown as follows:

Absolute value of complex viscosity (P) $|\rho^*|=|G^*|/\omega|G^*|=(G'^2+G''^2)^{1/2}$ wherein $|G^*|$: absolute value of complex modulus ($dyn/cm^2$)

$G'$: storage modulus ($dyn/cm^2$)

$G''$: loss modulus ($dyn/cm^2$)

$\omega$: angular frequency in the oscillation of paralell discs (rad/s).

Specifically, 2 ml of an aqueous suspension containing 0.1% of the homogenized BC is sandwiched between parallel discs having a diameter of 5 cm. Under the conditions of a temperature of 30° C. and strain of 10% in Frequency Sweep mode, the discs are oscillated at ten increasing steps of an angular frequency in the range of from 2 to 100 rad/s, and viscosity was then measured at an angular frequency of 10 rad/s. The strain is represented by the following equation:

Strain(%)$\gamma=R/H\times\theta\times100$ wherein R: radius of the parallel discs (mm)

H: thickness of the sample between the discs (mm)

$\theta$: angular displacement of the parallel discs (rad)

Production and Homogenization of Bacterial Cellulose (Reference Example)

(1) Preparation of a Seed Bacteria Solution (growth of bacteria)

The cellulose-producing bacteria were grown in a flask culture.

A Roux flask (750 ml volume) containing 100 ml of a base medium consisting of fructose (40 g/L), potassium phosphate (1.0 g/L), magnesium sulfate (0.3 g/L), ammonium sulfate (3 g/L), Bacto-Peptone (5 g/L) and lactic acid (1.4 ml/L) was inoculated with 1 ml of a cryopreserved bacteria solution of BPR 2001 (FERM BP-4545) at an initial pH of 5.0. The bacteria were incubated in an incubator at 28° C. for three days under a static culture condition. After the completion of the seed culture, the Roux flask was vigorously shaken and aseptically filtered through a gauze to obtain the seed bacteria solution.

(2) Production of Bacterial Cellulose in the Agitated Culture.

60 ml of the above seed bacteria solution was aseptically inoculated into 540 ml of a sterilized culture medium for the agitated culture in a small jar fermenter (1000 ml total volume). The bacteria were cultured at 30° C. for 20 or 30 hours and at an initial agitation rate of 400 rpm, while adjusting a pH to 5.0 by the addition of ammonia gas or 1N $H_2SO_4$ and maintaining an amount of dissolved oxygen (DO) between 3.0 and 21.0% by automatically controlling the agitation rate.

The following CSL-Fru medium was used for the agitated culture.

TABLE 1

CSL-Fru medium

| | |
|---|---|
| Fructose | 4.0 (%) |
| $KH_2POA$ | 0.1 |
| $MgSO_4.7H_2O$ | 0.25 |
| $(NH_4)_2SO_4$ | 0.33 |
| Vitamin Mixture (see below) | 1.0 |
| Salt Mixture (see below) | 1.0 |
| CSL (Corn Steep Liquor) | 2.0 |
| an initial pH of 5.0 | |

TABLE 2

Salt Mixture

| | | |
|---|---|---|
| $FeSO_4.7H_2O$ | 360 | mg/l |
| $CaCl_2.2H_2O$ | 1470 | mg/l |
| $Na_2MoO_2.2H_2O$ | 242 | mg/l |
| $ZnSO_4.7H_2O$ | 173 | mg/l |
| $MnSO_4.5H_2O$ | 139 | mg/l |
| $CuSO_4.5H_2O$ | 5 | mg/l |

TABLE 3

Vitamin Mixture

| compound | mg/L |
|---|---|
| Inositol | 200 |
| Niacin | 40 |
| Pyridoxine HCl | 40 |
| Thiamine HCl | 40 |
| Ca Pantothenate | 20 |
| Riboflavin | 20 |
| p-Aminobenzonic Acid | 20 |
| Folic Acid | 0.2 |
| Biotin | 0.2 |

After the completion of the culture, solid mass accumulated in the jar fermenter were collected and washed with water to remove the medium components. The solid mass were then washed with 1% NaOH aqueous solution at 80° C. for overnight to remove the bacteria. The solid mass were then neutralized with sulfuric acid and washed with water until its pH reached a neutral range to give a purified bacterial cellulose.

(3) Homogenization of Bacterial Celulose

The purified bacterial cellulose obtained in the above process (2) was mixed with water to prepare an aqueous suspension having a concentration of about 0.1% (dry weigh of BC/volume). The resulting suspension was subjected to homogenization by means of a blender (Oster blender manufactured by SUNBEAM-OSTER HOUSEHOLD PRODUCTS Co.) with a maxiumum rotational speed at 25° C. for 3 min.

The above concentration of BC was measured as follows:

Solid contents in a wet state were separated from the cluture broth by centrifugation, soaked at 100° C. for one hour in a 0.2 N NaOH solution of an amount of 20 times the separated solids contents to remove the bacterial cells and other culture ingredients from the bacterial cellulose, washed throughly, and dried. The thus dried BC was then weighed.

EXAMPLE 1

Suspension (800 L) containing 0.4% of the purified BC obtained in the Reference Example (2) was prepared and filtered through the following filter press:

(1) Characters of Filter Press:

Filter area of 2.67 m² (the size of a filer plate 750 mm×750 mm); Number of the filter rooms of 4; a press mechanism is provided; and filter plate and press membrane are made of polypyrene;

(2) Filtration Method:

Filtration under a constant pressure of 4 kg/cm²;

(3) Press Method:

Press pressure of 6 kg/cm² and pressure time of 20 min.

(4) Process Temperature of 60° C.

(5) Filter Cloth:

Made of Tetron with filtration rate of 30 cc/cm²/sec.

After the completion of the filtration, BC was subjected to a pressing step for 20 min. to give cake containing 25.8 to 29.3% BC, from which no water squeezed out. The pressed BC was very easily peeled off the filter cloth and substantial no BC remained attached to the filter. Accordingly, it was very easy to handle in transportation.

COMPARATIVE EXAMPLE 1

The cake containing 12.5 to 14% BC was prepared according to Example 1, only with the exception that the pressing time was reduced to 5 min. This cake was solid in a plate shape, but much softer than that obtained in Example 1. Thus, it was transformed upon the press by fingers. Leakage of a litte of water from the cake was observed. The pressed BC was hardly peeled off the filter cloth and a significant amount of BC remained attached to it. The plate-shape of the BC cake could not be maintained during transportation due to its softness.

EXAMPLE 2

Suspension (800 L) containing 0.4% of the purified BC was prepared under the same conditions as Example 1, and subjected to homogenization with an ultrasonic homogenizer under the following conditions:

Sonorater (SONIC CO.); Concentration during the homogenization of 0.4% (dry weigh of BC/volume); Temperature of 25° C.; flow rate of 6 L/min; pressure of 50 kg/cm²; and passage number of one. The positions of a back-pressure valve and a blade were adjusted so as to obtain a maximum sonic pressure.

The homogenized BC was served as feed in the same filtration and pressing operations as in Example 1 to give cake containing 27.3 to 29% BC and the same properties as in Example 1. On the other hand, the cake containing 12.5 to 14% BC showed the same properties as in Comparative Example 1.

EXAMPLE 3

Using the homogenized BC according to Example 2, the cake with various BC concentrations was prepared by means of different kinds of solid-liquid separators. The results are shown in TABLE 4.

TABLE 4

| Solid-liquid separator | BC concentration | Shape |
| --- | --- | --- |
| Screw decanter centrifuge | 3–10% | paste |
| Bucket-type centrifuge | 2–15% | paste |
| Disk-type centrifuge | 0.4–0.6% | paste |
| Filter press | 26–30% | plate |

When BC was concentrated by means of a filter press, the resulting palte-formed BC could be easily transported.

EXAMPLE 4

The BC suspension homogenized according to Reference Example (3) was concentrated by means of a laboratory-type centrifuge (Hitachi CR5DL) to a paste-state, and pressed between a pair of handmade filter paper to a final concentration of 6%, 10% and 30%, respectively, The concentrated BC was again diluted by mixing it with water to 4%, and re-dispersed by a blender (Oster blender manufactured by SUNBEAM-OSTER HOUSEHOLD PRODUCTS Co.) at 25° C. for 30 seconds. The rotation rate of the agitator was adjusted to a minimum level.

Evaluation

1. Yield on Fillers:

100 parts of light calcium carbonate and 1 part of cationic starch were added to 100 parts of a pulp which had been obtained by mixing the samples of the bacterial cellulose with LBKP homogenized in accordance with JIS-P-8209 at a weight ratio of 2.5:97.5. Yield on the fillers was determined from an amount of those that had passed through a filter in accordance with TAPPI standard method T261. The weight of the fillers was measured by ashing them at 400 ° C. for 8 hours in accordance with TAPPI standard method T269.

2. Freeness:

The BC samples and LBKP homogenized in accordance with JIS-P-8209 were mixed at a weight ratio of 5:95 to measure a Canadian Standard Freeness (CSF) in accordance with JIS-P-8121.

TABLE 5

|  |  | Yield on fillers (%) | Freeness (cc) |
| --- | --- | --- | --- |
| Example: | Concentrated to 6% & Re-dispers ion | 38.4 | 300 |
|  | Concentrated to 10% & Re-dispersion | 38.5 | 310 |
|  | Concentrated to 30% & Re-dispersion | 38.0 | 310 |
| Comparative Example: | Only homogenization (no concentration) | 38.7 | 250 |

Owing to the concentration of the homogenized BC and re-dispersion, freeness of the concentrated and re-dispersed BC was improved and its yield on fillers was substantially the same as that of the original homogenized BC.

EXAMPLE 5

The BC suspension containing about 6% of BC and about 94% of water was prepared by concentrating the purified BC obtained in Reference Example (2) with a centrifugal. The concentrated BC was then aspirated and dried in the atmosphere at 60° C. to give the concentrated BC having different kinds of concentration. Each concentrated BC was then mixed with water and sufficiently agitated to give suspension (dispersion) of 0.2% of BC concentration. The resulting suspension (10 ml) was homogenized by means of Phy-scotron (Niti-on Medical & Physical Instruments Mfg. Co.) for 5 min. The resulting suspension of the homogenized BC was subjected to the measurement of precipitation degree.

The results are shown in TABLE 6.

TABLE 6

| BC concentration in the concentrate before suspension into water (%) | Precipitation degree (%) |
| --- | --- |
| 6.1 | 27 |
| 12.2 | 30 |
| 27.3 | 32 |

TABLE 6-continued

| BC concentration in the concentrate before suspension into water (%) | Precipitation degree (%) |
|---|---|
| 53.3 | 32 |
| 58.4 | 31 |
| 84.2 | 20 |

The present BC concentrate containing BC of 10% or more, preferably 26% or more and less than 75% showed higher values in precipitation degree than that of the unconcentrated BC (6.1% BC) after re-suspension into water and homogenization. It is found that the present BC concentrate is preferred material for providing homogenized BC with superior dispersibility and suspensibility.

EXAMPLE 6

The BC suspension containing about 6% of BC and about 94% of water prepared in Example 5 was diluted with water to a final BC concentration of 0.5%, and the resulting suspension (250 ml) was homogenized by a mixer at 18,000 rpm for one min. The thus homogenized BC suspension (30 ml, BC concentration of 0.5%) was concentrated by means of the combination of an aspirator and IR dryer to give the concentrated BC having different kinds of BC and water concentration. Then, each BC concentrate was mixed with water to a final BC concentration of 0.2%, sufficiently agitated and dispersed, and finally homogenized by the same ultrasonic homogenizer as in Example 2 for 1 min. The precipitation degree of each homogenized BC was determined. The resutls are shown in TABLE 7.

TABLE 7

| BC concentration in the cendentrate before suspension into water (%) | Precipitation degree (%) |
|---|---|
| 0.5 | 50 |
| 4.8 | 56 |
| 10.7 | 66 |
| 21.7 | 68.5 |
| 30.0 | 64.5 |
| 36.8 | 64 |
| 39.4 | 65 |
| 50.0 | 61 |
| 60.0 | 60.5 |

The present BC concentrate containing BC of 4.8% or more, preferably 10% or more, more preferably 20% or more and less than 80% showed higher values in precipitation degree than that made of the unconcentrated BC (0.5% BC) after re-suspension into water and homogenization. It is found that the present BC concentrate is preferred material for providing homogenized BC with superior dispersibility and suspensibility. These effects by the concentration are much more significant than those in Example 5.

EXAMPLE 7

The BC suspension having three kinds of BC concentration was prepared, re-dispersed and homogenized as in Example 5. Their precipitation degree and viscosity were determined. The results are shown in TABLE 8.

TABLE 8

| BC concentration in the cendentratebefore suspension into water (%) | Precipitation degree (%) | Viscosity (poise) |
|---|---|---|
| 6.1 | 23 | 9.5 |
| 18.1 | 28 | 14.0 |
| 27.0 | 31 | 17.5 |

The present BC concentrate containing BC of 10% or more, preferably 20% or more showed a higher value in precipitation degree than that of the unconcentrated BC (6.1% BC) after re-suspension into water and homogenization. It is found that the present BC concentrate is preferred material for providing homogenized BC with superior dispersibility and suspensibility as well as excellent viscosity.

EXAMPLE 8

The BC suspension containing about 6% of BC and about 94% of water prepared in Example 5 was diluted with water to a final BC concentration of 0.1%, and the resulting suspension (1000 ml) was homogenized by a blender (Oster blender manufactured by SUNBEAM-OSTER HOUSEHOLD PRODUCTS Co.) at a maximum level for 5 min. The thus homogenized BC suspension was concentrated by centrifugation at 18,000 rpm for 2 min. to a final BC concentration of 3.00%. The same homogenized BC suspension was concentrated by aspiration to a final BC concentration of 15.60%. Then, each BC concentrate (35 ml) was mixed with water to a final BC concentration of 0.1%, and sufficiently homogenized by a mixer (Excelhomogenizer, Nihon Seiki Co,) at 18,000 rpm for 5 min. The viscosity of each homogenized BC was determined. The resutls are shown in TABLE 9.

TABLE 9

| BC concentration in the original homogenizationor concentrate before homogenization by mixer (%) | Viscosity (poise) |
|---|---|
| 0.1 | 6.12 |
| 3.00 | 9.06 |
| 15.60 | 9.96 |

It is found that by concentrating the homogenized BC, again diluting it to an aqueous suspension (dispersion) followed by a futher homogenization, it will be possible to obtain the homogenized BC having a higher viscosity than the homogenized BC prepared without concentration.

What is claimed is:

1. An aqueous bacterial cellulose concentrate containing homogenized bacterial cellulose in an amount of the range between 4% by weight and less than 75% by weight and more than 25% by weight water.

2. An aqueous bacterial cellulose concentrate containing homogenized bacterial cellulose in an amount of the range between 10% by weight and less than 75% by weight and more than 25% by weight water.

3. A method for the improvement of dispersibility and suspendability of bacterial cellulose, comprising concentrating an aqueous suspension of bacterial cellulose to a final concentration of bacterial cellulose of between 10% by weight and less than 75% by weight, dispersing the concentrated bacterial cellulose into an aqueous solution and homogenizing the bacterial cellulose in the resulting dispersion.

4. An aqueous suspension of bacterial cellulose prepared according to the method of claim 3.

5. A method for the improvement of paper-making properties of bacterial cellulose, comprising concentrating an aqueous suspension of homogenized bacterial cellulose to a final concentration of the bacterial cellulose of between 4% by weight and less than 75% by weight, dispersing the concentrated bacterial cellulose into an aqueous solution and homogenizing the bacterial cellulose in the resulting dispersion.

6. An aqueous suspension of bacterial cellulose prepared according to the method of claim 5.

7. The aqueous bacterial cellulose concentrate of claim 1, containing 20% to less than 75% by weight of the bacterial cellulose.

8. The aqueous bacterial cellulose concentrate of claim 1, containing 26% to less than 75% by weight of the bacterial cellulose.

9. The aqueous bacterial cellulose concentrate of claim 1, containing 30% to less than 75% by weight of the bacterial cellulose.

* * * * *